United States Patent [19]

Jan et al.

[11] 4,145,217
[45] Mar. 20, 1979

[54] QUINOXALINES AND THEIR USE IN PHOTOGRAPHIC PROCESSES

[75] Inventors: Gerald Jan; Remon Hagen; John Lenoir, all of Marly, Switzerland

[73] Assignee: Ciba-Geigy AG, Basel, Switzerland

[21] Appl. No.: 799,033

[22] Filed: May 20, 1977

[30] Foreign Application Priority Data

May 24, 1976 [CH] Switzerland .................. 6520/76

[51] Int. Cl.² .................. G03C 7/00; G03C 5/32
[52] U.S. Cl. .................. 96/53; 96/60 R
[58] Field of Search .................. 96/53, 73, 20, 60 R

[56] References Cited

U.S. PATENT DOCUMENTS

| | | | |
|---|---|---|---|
| 2,221,793 | 11/1940 | Gaspar | 96/53 |
| 3,656,953 | 4/1972 | Schlunke et al. | 96/53 |
| 3,767,402 | 10/1973 | Schlunke et al. | 96/53 |
| 3,769,576 | 3/1974 | Schlunke et al. | 96/53 |
| 3,963,492 | 6/1976 | Marthaler et al. | 96/53 |
| 4,014,698 | 3/1977 | Marthaler et al. | 96/53 |

*Primary Examiner*—Mary F. Kelley
*Attorney, Agent, or Firm*—Sprung, Felfe, Horn, Lynch & Kramer

[57] ABSTRACT

Quinoxalines of the formula

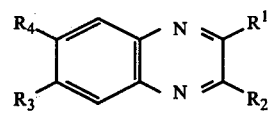

are provided, in which $R_1$ is hydrogen if $R_3$ and $R_4$ conjointly are $-O(CH_2)_pO-$, or is $-CH_2OR$, $-CH_2NRR'$, $-CH_2OCOR$, $-CH_2Cl$, $-CH_2Br$, $-CH_2CN$, $-CH_2SR$, $-CH_2SCN$, $-CH_2O(CH_2)_mOR$, $-CH_2(OCH_2CH_2)_nOR$, $-CH_2SO_2R_5$, $-CH_2PO(OR_5)_2$, $-CH_2SO_3R_6$ or $-CH_2PO(OR_6)_2$ and $R_2$ is lower alkyl, $-CH_2PO(OR_5)_2$, $-CH_2PO(OR_6)_2$ or $CH_2SO_3R_6$, $R_3$ and $R_4$ independently are lower alkyl, lower alkoxy, $RO(CH_2)_mO-$ or $RO(CH_2CH_2O)_n-$ or $R_3$ and $R_4$ conjointly are $-O(CH_2)_pO-$, R and R' independently are hydrogen or lower alkyl, $R_5$ is lower alkyl, $R_6$ is hydrogen, an alkali metal cation or $-N^{\oplus}(R)_4$, m is 3 or 4, n is 1 to 3 and p is 1 or 2.

The quinoxalines are useful as bleach catalysts, especially as dye bleach catalysts, in processing baths for the photographic silver dye bleach process.

9 Claims, No Drawings

QUINOXALINES AND THEIR USE IN PHOTOGRAPHIC PROCESSES

The present invention relates to new quinoxalines of the formula

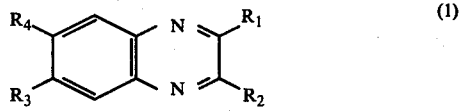

in which $R_1$ is hydrogen if $R_3$ and $R_4$ conjointly are —O(CH$_2$)$_p$O—, or is —CH$_2$OR, —CH$_2$NRR', —CH$_2$OCOR, —CH$_2$Cl, —CH$_2$Br, —CH$_2$CN, —CH$_2$SR, —CH$_2$SCN, —CH$_2$O(CH$_2$)$_m$OR, —CH$_2$(OCH$_2$CH$_2$)$_n$OR, —CH$_2$SO$_2$R$_5$, —CH$_2$PO(OR$_5$)$_2$, —CH$_2$SO$_3$R$_6$ or —CH$_2$PO(OR$_6$)$_2$ and $R_2$ is alkyl with 1 to 5 carbon atoms, —CH$_2$PO(OR$_5$)$_2$, —CH$_2$PO(OR$_6$)$_2$ or CH$_2$SO$_3$R$_6$, $R_3$ and $R_4$ independently are alkyl with 1 to 5 carbon atoms, alkoxy with 1 to 4 carbon atoms, RO(CH$_2$)$_m$O— or RO(CH$_2$CH$_2$O)$_n$— or $R_3$ and $R_4$ conjointly are —O(CH$_2$)$_p$O—, R and R' independently are hydrogen or alkyl with 1 to 4 carbon atoms, $R_5$ is alkyl with 1 to 4 carbon atoms, $R_6$ is hydrogen, an alkali metal cation or —N$^\oplus$(R)$_4$, m is 3 or 4, n is 1 to 3 and p is 1 or 2.

The radical $R_1$ is hydrogen only when the radicals $R_3$ and $R_4$ conjointly are —OCH$_2$O— or —OCH$_2$CH$_2$O— members, that is to say together with the benzene ring form a dioxolo or dioxano ring. If $R_1$ represents a radical which contains R or R' as further substituents, these substituents as a rule denote hydrogen or straight-chain or branched alkyl with 1 to 4 carbon atoms, so that $R_1$ can be, for example —CH$_2$OH, —CH$_2$OCH$_3$, —CH$_2$OC$_2$H$_5$, —CH$_2$OC$_3$H$_7$ (n- and iso-), —CH$_2$OC$_4$H$_9$, —CH$_2$NH$_2$, —CH$_2$N(CH$_3$)$_2$, —CH$_2$NHC$_4$H$_9$, —CH$_2$OCOH, —CH$_2$OCOCH$_3$, —CH$_2$OCOC$_2$H$_5$, —CH$_2$OCOC$_4$H$_9$, —CH$_2$SH, —CH$_2$SCH$_3$, -CH$_2$SC$_2$H$_5$, —CH$_2$SC$_3$H$_7$, CH$_2$SC$_4$H$_9$; —CH$_2$O(CH$_2$)$_3$OH, —CH$_2$O(CH$_2$)$_3$OCH$_3$, —CH$_2$O(CH$_2$)$_4$OCH$_3$, —CH$_2$O(CH$_2$)$_3$OC$_2$H$_5$, —CH$_2$O(CH$_2$)$_3$OC$_4$H$_9$; —CH$_2$OCH$_2$CH$_2$OH, —CH$_2$(OCH$_2$CH$_2$)$_2$OH, —CH$_2$OCH$_2$CH$_2$OCH$_3$, —CH$_2$OCH$_2$CH$_2$OC$_2$H$_5$, —CH$_2$OCH$_2$CH$_2$OC$_3$H$_7$ or —CH$_2$OCH$_2$CH$_2$OC$_4$H$_9$. The substituent $R_5$ can be straight-chain or branched alkyl with 1 to 4 carbon atoms, so that, for example, —CH$_2$SO$_2$CH$_3$, CH$_2$SO$_2$C$_2$H$_5$, —CH$_2$SO$_2$C$_3$H$_7$, —CH$_2$SO$_2$C$_4$H$_9$ and also —CH$_2$PO(OCH$_3$)$_2$, —CH$_2$PO(OC$_2$H$_5$)$_2$, —CH$_2$PO(OC$_3$H$_7$)$_2$ or —CH$_2$PO(OC$_4$H$_9$)$_2$ are possible as further radicals $R_1$. As well as hydrogen, the substituent $R_6$ can be an alkali metal cation, for example a lithium, sodium or potassium cation, as well as an ammonium radical, such as, for example, —N$^\oplus$H$_4$ or —N$^\oplus$(CH$_3$)$_4$.

Those radicals $R_1$ in which R and R' are hydrogen or methyl, $R_5$ is methyl and $R_6$ is hydrogen, a sodium or potassium cation or —N$^\oplus$H$_4$ are preferred. Further radicals $R_1$ are —CH$_2$SCN as well as, in particular, —CH$_2$Cl, —CH$_2$Br and —CH$_2$CN.

If $R_2$ is alkyl, possible radicals are straight-chain and branched radicals, such as, for example, methyl, ethyl, propyl, isopropyl, butyl and isobutyl, whilst $R_5$ and $R_6$ in the radicals —CH$_2$PO(OR$_5$)$_2$, —CH$_2$PO(OR$_6$)$_2$ and —CH$_2$SO$_3$R$_6$ have the indicated meanings.

Alkyl radicals for $R_3$ and $R_4$ can be the same radicals as have been mentioned for $R_2$ and the amyl or isoamyl radical may also be mentioned as an alkyl radical with 5 carbon atoms.

The alkoxy radicals can be, for example, methoxy, ethoxy, propoxy and butoxy, whilst for RO(CH$_2$)$_m$O— and RO(CH$_2$CH$_2$O)$_n$— the same substituents and values for the indices as have been mentioned in the definition of $R_1$ can be employed. $R_3$ and $R_4$ can also form, together with the carbon atoms to which they are bonded, a 5-membered or 6-membered ring containing two oxygen atoms, depending on whether p is 1 or 2 and the molecule part necessary for cyclisation is thus —OCH$_2$O— or —OCH$_2$CH$_2$O—.

Those quinoxalines of the formula (1) in which $R_3$ and $R_4$ independently are alkyl with 1 to 5 carbon atoms or alkoxy with 1 to 4 carbon atoms, or $R_3$ and $R_4$ conjointly are —O(CH$_2$)$_p$O—, and $R_1$, $R_2$ and p have the indicated meanings are now preferred.

The quinoxalines of the formula

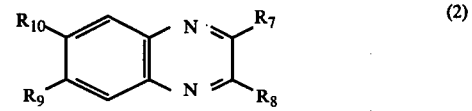

in which $R_7$ is hydrogen if $R_9$ and $R_{10}$ conjointly are —O(CH$_2$)$_p$O— or is —CH$_2$OR$_{11}$, —CH$_2$NR$_{11}$R'$_{11}$, —CH$_2$OCOR$_{11}$, —CH$_2$OCH$_2$CH$_2$OR$_{11}$, —CH$_2$SO$_3$R$_6$, —CH$_2$Br, —CH$_2$SR$_{11}$, —CH$_2$SO$_2$CH$_3$, —CH$_2$PO(OCH$_3$)$_2$ or —CH$_2$PO(OR$_6$)$_2$ and $R_8$ is methyl or —CH$_2$SO$_3$R$_6$, $R_9$ and $R_{10}$ independently are alkoxy with 1 to 4 carbon atoms, or $R_9$ and $R_{10}$ conjointly are —O(CH$_2$)$_p$O—, $R_{11}$ and R'$_{11}$ are hydrogen or methyl and $R_6$ and p have the indicated meanings are of particular interest.

Quinoxalines which are very particularly suitable also correspond to the formula

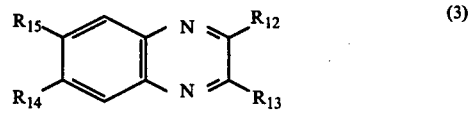

in which $R_{12}$ is hydrogen if $R_{14}$ and $R_{15}$ conjointly are —O(CH$_2$)$_p$O— or is —CH$_2$OH or —CH$_2$SO$_3$R$_6$ and $R_{13}$ is methyl or —CH$_2$SO$_3$R$_6$, $R_{14}$ and $R_{15}$ are methoxy, or $R_{14}$ and $R_{15}$ conjointly are —O(CH$_2$)$_p$O—, and $R_6$ and p have the indicated meanings.

The quinoxalines of the formula (1) are appropriately manufactured in a manner which is in itself known (in this context compare J. C. E. Simpson, Condensed Pyridazine and Pyrazine Rings, in A. Weissberger, The Chemistry of Heterocyclic Compounds, J. Wiley & Sons, New York 1953, 203 et seq.; A. R. Katritzky, Advances in Heterocyclic Chemistry Volume 2, in G. W. H. Cheeseman, Recent Advances in Quinoxaline Chemistry, Academic Press, New York and London 1963, 203 et seq. and Y. T. Pratt, The Quinoxalines, in R. C. Elderfield, Heterocyclic Compounds Volume 6, J. Wiley & Sons, New York 1957, 455 et seq.) by a condensation reaction of an aromatic 1,2-diamine with a 1,2-dicarbonyl compound. In place of the diamine, it is also possible to use the corresponding, considerably more stable o-nitroaniline or the corresponding o-dinitro compound or a corresponding o-arylazoaniline, which can be reduced to the desired diamine and then reacted, without intermediate isolation, to give the quinoxaline. Corresponding substituted benzfuroxanes and their reduction products (benzfurazanes) can also be reduced via intermediate stages to 1,2-diamines (F. B. Mallory & S. P. Varimibi, J. Org. Chemistry 28, 1,656 et seq. (1963)) and the diamines thus accessible subjected to a condensation reaction to give quinoxalines. In place of the 1,2-dicarbonyl compound, α-oximinoketones can also be reacted with 1,2-diamines to give quinoxalines (in this context compare J. C. E. Simpson, loc. cit.).

It has proved advantageous to manufacture quinoxalines of the formula (1), in which the radicals $R_1$ and $R_2$ do not contain a halogen atom from the corresponding halogenomethyl compounds or di-(halogenomethyl) compounds by replacing the halogen atoms, using suitable Lewis bases. Examples of Lewis bases which can be used are: primary and secondary amines, mercaptides, thiourea derivatives, alcoholates, phosphite sulphites, hydroxy compounds (hydroxides), cyanides and anions of carboxylic acids or sulphinic acids.

The present invention also relates to a process for the manufacture of quinoxalines of the formula (1). The process is characterised in that aromatic diamines of the formula

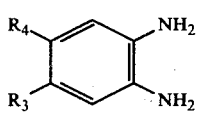 (4)

in which $R_3$ and $R_4$ have the indicated meanings, are subjected to a condensation reaction with 1,2-dicarbonyl compounds of the formula

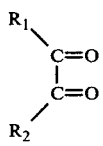 (5)

or α-oximinoketones of the formula

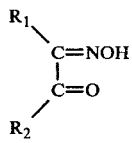 (6)

in which $R_1$ and $R_2$ have the indicated meanings.

The condensation reaction is generally carried out in a solvent, such as, for example, glacial acetic acid, ethyl acetate, ethanol, water or 2-methoxyethanol, at temperatures of 5° C. to 100° C.

With this process the new compounds as a rule precipitate out when the reaction mixture is cooled after the end of the reaction; otherwise they are obtained in good yield by distilling off the solvent and filtering off, as well as optionally recrystallising or purifying by chromatography.

The manufacture of the quinoxalines of the formula (2) is carried out as indicated by subjecting an aromatic diamine of the formula

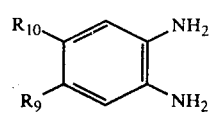 (7)

to a condensation reaction with a 1,2-dicarbonyl compound of the formula

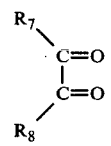 (8)

or with an α-oximinoketone of the formula

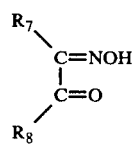 (9)

The radicals $R_7$, $R_8$, $R_9$ and $R_{10}$ have the indicated meanings.

For the manufacture of the quinoxalines of the formula (3), diamines of the formula

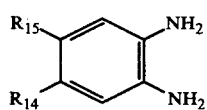 (10)

are correspondingly reacted with 1,2-dicarbonyl compounds or α-oximinoketones of the formulae

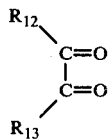 (11)

and

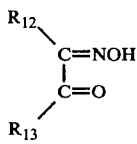 (12)

The radicals $R_{12}$, $R_{13}$, $R_{14}$ and $R_{15}$ have the indicated meanings.

In place of the 1,2-dicarbonyl compounds or the α-oximinoketones of the formulae (5), (6), (8), (9), (11) and (12), it is possible, in particular, to employ the corresponding halogeno compounds

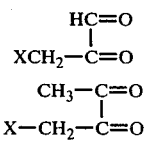

(13a)

(13b)

-continued $$XCH_2-C=O \atop XCH_2-C=O \quad (14)$$

$$HC=NOH \atop XCH_2-C=O \quad (15)$$

and $$XCH_2-C=NOH \atop XCH_2-C=O \quad (16)$$

in which X is preferably chlorine or bromine, and subsequently, to introduce the corresponding radicals for $R_1$, $R_2$, $R_7$, $R_8$ and $R_{12}$ and $R_{13}$, with the exception of —$CH_2Cl$ and —$CH_2Br$ into the molecule by replacing the halogen atoms.

The quinoxalines can be obtained in better yield and higher purity if the condensation reaction is carried out in a nitrogen atmosphere.

Examples of starting materials which can be used for one of the said syntheses are the compounds named below:

1,2-Dicarbonyl compound, α-oximinoketones

Methylglyoxal, 1,4-dibromo-butane-2,3-dione, 1-bromobutane-2,3-dione, 1-acetoxy-butane-2,3-dione, 1-methoxy-butane-2,3-dione, 1-thiomethoxy-butane-2,3-dione, ethylglyoxal, propylglyoxal, butylglyoxal, oximimo-2-acetone, 1-oximino-2-butanone, 1-oximino-2-hexanone and 1-oximino-2-pentanone.

Lewis bases

Sodium methylate, sodium ethylate, potassium methylate, potassium ethylate, potassium propylate, potassium isopropylate, potassium butylate, potassium isobutylate, potassium tertiary butylate, sodium mercaptide, potassium mercaptide, sodium methylmercaptide, potassium methylmercaptide, sodium ethylmercaptide, potassium ethylmercaptide, thiourea, potassium xanthate, sodium acetate, potassium acetate, sodium propionate, potassium propionate, sodium 3-methoxypropylate, potassium 3-methoxypropylate, sodium 4-methoxybutylate, potassium 4-methoxybutylate, potassium 2-methoxyethylate, sodium 2-ethoxyethylate, potassium 2-ethoxyethylate, sodium cyanide, potassium cyanide, sodium monotetramethyleneglycolate, potassium monotetramethyleneglycolate, sodium monotrimethyleneglycolate, potassium monotrimethyleneglycolate, sodium monoglycolate, potassium monoglycolate, sodium cyanide, potassium thiocyanate, sodium methylsulphinate, potassium methylsulphinate, sodium ethylsulphinate, potassium ethylsulphinate, ammonia, dimethylamine, potassium phthalimide, guanidine, diethylamine, dipropylamine, methylamine, ethylamine, propylamine, sodium sulphite, potassium sulphite, water, sodium hydroxide, potassium hydroxide, trimethyl phosphite, triethyl phosphite, tributyl phosphite and tripropyl phosphite.

o-Nitroanilines and o-dinitrobenzenes and 1,2-diamines 4,5-Dimethoxy-1,2-dinitrobenzene, 4-amino-5-nitroveratrole, 4,5-diamino-veratrole, 4,5-diethoxy-1,2-dinitrobenzene, 4-amino-1,2-diethoxy-5-nitrobenzene, 1,2-diamino-4,5-diethoxy-benzene, 5,6-dinitro-benzo-1,3-dioxole, 5-amino-6-nitro-benzene-[d]-dioxole-1,3, 5,6-diamino-benzo-d]-dioxole-1,3, 2,3-dihydro-6,7-dinitro-benzene-1,4-dioxine, 6-amino-2,3-dihydro-7-nitro-benzo-1,4-dioxine, 6,7-diamino-2,3-dihydro-benzo-[b]-dioxine-1,4 1,2-diamino-4,5-dimethylbenzene, 1-amino-4,5-dimethyl-2-nitrobenzene and 4,5-dimethyl-1,2-dinitrobenzene.

The quinoxalines of the formula (1) can be used in a processing bath, preferably an acid bleach bath, as bleach catalysts for the silver dye bleach process and especially in an acid dye bleach bath as dye bleach catalysts.

They are particularly readily soluble in acid baths and have an excellent action as dye bleach catalysts. They can be used either on their own or in the presence of other customary dye bleach ctalysts. It is also possible for different quinoxalines of the formula (1) to be employed at the same time in the dye bleach bath. Finally, it is also possible to employ the quinoxalines of the formula (1) together with other measures which promote dye bleaching, such as, for example, by adding organic solvents or bleaching accelerators. Moreover, it is also possible to employ the quinoxalines of the formula (1) as dye bleach catalysts in a layer of the photographic material.

The quinoxalines of the formula (1) are, furthermore, also suitable for processes for the production of coloured photographic images by the silver dye bleach process as well as also for processes for rapid processing of silver dye bleach materials. In these processes, for example, the dye bleach bath, the silver bleach bath and, optionally, also the fixing bath are combined.

As a rule, these combined baths then contain bleaching accelerators, such as, for example, phosphines, oxidising agents and antioxidants (compare DT-OS 2,448,433) in addition to the said quinoxalines.

The present invention thus also relates to a process for the production of coloured photographic images by the silver dye bleach process on materials which contain, on a substrate, at least one silver halide emulsion layer with a dyestuff which can be bleached imagewise, by exposure and subsequent processing by developing the silver image, dye bleaching, silver bleaching, silver fixing and washing, wherein the dye bleaching and/or silver bleaching is carried out in the presence of at least one quinoxaline of the formula (1) as the bleach catalyst, as well as also to a process for the rapid processing of silver dye bleach materials which comprises the following process steps (1) silver developing, (2) dye bleaching and silver bleaching, (3) silver fixing and (4) washing.

The latter process is characterised in that, using treatment baths corresponding to the treatment stages (1) to (4), and using them in the sequence (1) to (4), a bleach bath which contains (a) a strong acid, (b) a water-soluble iodide, (c) a water-soluble oxidising agent, (d) an antioxidant and, (e) as the bleach catalyst, a quinoxaline of the formula (1), preferably in an amount of 0.5 to 5 g per litre, and (f) optionally a bleach accelerator is used for the combined dye bleaching and silver bleaching (2) and that the entire processing, from entry into the first bath (1) to leaving the final bath, is carried out at temperatures of 20° to 90° C.

Moreover, the processing can also be so carried out that the entire processing, from entry into the first bath (1) to leaving the final bath, takes at most 10 minutes and the dwell time in the individual baths is at most 2 minutes.

The invention also relates to photographic processing baths, especially dye bleach baths or combined dye bleach and silver bleach baths, for the silver dye bleach process which contain, as the bleach catalyst, at least one quinoxaline of the formula (1). In general, the aqueous dye bleach formulations required for the processing are allowed to act on the material in the form of dilute aqueous solutions which contain components (a) to (e) and, optionally, (f).

However, other methods, for example use in paste form, are also conceivable. The temperature of the baths during processing, and especially also the temperature of the bleach bath, can in general be between 20° and 60° C. and, of course, the requisite processing time is shorter at a higher temperature than at a lower temperature.

The aqueous bleaching formulation according to the present invention can also be prepared in the form of a liquid concentrate, especially an aqueous concentrate, and, because of its good stability, can be stored for a prolonged period. It is advantageous to use, for example, two liquid concentrates, of which one contains the strong acid (a) and the oxidising agent (c) and the other contains the remaining components (b), (d), (e) and, optionally, (f), it being possible to add an additional solvent, such as ethyl alcohol or propyl alcohol, ethylene glycol methyl ether or ethylene glycol ethyl ether, to the latter concentrate in order to improve the solubility, especially of component (e).

These concentrates can optionally be diluted by dilution with water or with a mixture of water and an organic solvent.

For silver developing in process step (1) it is possible to use baths of customary composition, for example those which contain hydroquinone and, if desired, additionally 1-phenyl-3-pyrazolidinone, as the developer substance.

The bleach bath (2) preferably contains sulphuric acid or sulphamic acid as the strong acid. The pH value of the bleach bath (2) is, in particular, not greater than 2 and preferably not greater than 1. The water-soluble iodides are as a rule alkali metal iodides, especially sodium iodide and potassium iodide. The amount of iodide is about 2 to 50 g/l of bleach bath.

Water-soluble, aromatic nitro and dinitro compounds are appropriately used as the oxidising agent. The use of such oxidising agents with a view to thus influencing the colour balance and the contrast in the images produced by the dye bleach process has already been described in German Patent Specification 735,672, in British Patent Specification 539,190 and 539,509 and in Japanese Patent Publication 22,673/69.

Particularly advantageous oxidising agents are the compounds of the formula

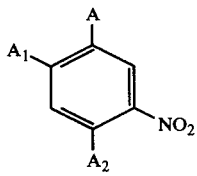

(17)

in which A is $—CO_2M$ or $—SO_3M$, $A_1$ is hydrogen, hydroxyl, amino($NH_2$), methyl or methoxy, $A_2$ is hydrogen, methyl, methoxy or trifluoromethyl and M is hydrogen, an alkali metal cation or $—N(R)_4$, in which R has the indicated meaning.

Examples of oxidising agents which can be used are the following aromatic nitro compounds: 3-nitrobenzenesulphonic acid, 3-nitrobenzoic acid, 2-amino-5-nitrobenzoic acid, 2-amino-5-nitrobenzenesulphonic acid, 2-amino-4-methyl-5-nitrobenzenesulphonic acid, 2-amino-4-methoxy-5-nitrobenzenesulphonic acid, 4-nitrophenol-2-sulphonic acid, 2-hydroxy-5-nitrobenzoic acid, 5-methyl-4-nitrophenol-2-sulphonic acid, 4-nitrotoluene-2-sulphonic acid, 4-nitroanisole-2-sulphonic acid, 2,4-dimethyl-5-nitrobenzenesulphonic acid, 5-methyl-4-nitro-anisole-2-sulphonic acid and 2-nitrotoluene-4-sulphonic acid; the following products can also be used: 2-amino-4-trifluoromethyl-5-nitrobenzenesulphonic acid, 2-amino-3-methyl-5-nitrobenzenesulphonic acid, 2-amino-3-methoxy-5-nitrobenzenesulphonic acid, 2-amino-5-methoxy-3-nitrobenzenesulphonic acid, 3-amino-4-methyl-5-nitrobenzenesulphonic acid, 2,4-diamino-5-nitrobenzenesulphonic acid, 2-amino-4-nitrobenzenesulphonic acid, 2-amino-5-methoxy-4-nitrobenzenesulphonic acid, 3-amino-4-methoxy-6-nitrobenzenesulphonic acid, 2-amino-5-methyl-3-nitrobenzenesulphonic acid, 3-nitro-aniline, 2-methyl-4-nitroaniline, 3-amino-7-nitronaphthalene-1,5-disulphonic acid, 2-amino-4-nitrophenol-6-sulphonic acid, 2-nitrophenol-4-sulphonic acid, 2-nitroanisole-4-sulphonic acid, 4-chloro-3-nitrobenzenesulphonic acid, 2-chloro-5-nitrobenzenesulphonic acid, 2,4-dinitrobenzenesulphonic acid, 2,6-dinitrotoluene-4-sulphonic acid, 2,4-dimethyl-3-nitrobenzenesulphonic acid, 2,4,6-trimethyl-3-nitrobenzenesulphonic acid, 2-amino-4-chloro-5-nitrobenzenesulphonic acid, 2-amino-3-chloro-5-nitrobenzenesulphonic acid, 2-nitrobenzoic acid, 3-nitrophthalic acid, 4-nitrophthalic acid, 3-[3'-nitrophenoxy]-propanesulphonic acid and (2'-dimethylamino)-ethyl 4-nitrobenzoate.

The nitrobenzenecarboxylic acids or nitrobenzenesulphonic acids can be employed either in the form of free acids or in the form of their metal salts, especially in the form of the alkali metal salts or alkaline earth metal salts, or in the form of ammonium salts.

The amount of oxidising agent in the bleach bath can be in the range from 1 to 30 g/l.

Organic mercapto compounds are advantageously used as antioxidants. It has proved particularly advantageous to use the compounds of the formulae

or

in which q denotes an integer with a value of 2 to 12, B denotes a sulphonic acid group or carboxylic acid group and m denotes one of the numbers 3 and 4. Mercapto compounds which can be used as antioxidants are described in DT-OS 2,258,076 and in DT-OS 2,423,814. Other antioxidants are e.g. thioglycerol or thiomalic acid or reductones such as ascorbic acid (U.S. Pat. No. 3,620,744). The amount of antioxidant is about 0.5 to 10 g/l.

The pH value of the bleach bath (2) should be less than 2 and this can be achieved without difficulty by the presence of sulphuric acid or sulphamic acid, which have already been mentioned. The temperature of the bleach bath, and also of the other treatment baths, is 20° to 90° C. In general it is advantageous to work at temperatures of not more than 60° C. The ratios of the substances (a), (b), (c) and (d) present in the bleach bath can vary within rather wide limits and are appropriately chosen analogously to the ratios for known methods. It is advantageous if the bleach baths contain the indicated, relatively high amount of 0.5 to 5 g of bleach catalyst per litre of bath liquid.

The silver fixing bath can be of known and customary composition. The fixer used is, for example, sodium thiosulphate or, advantageously, ammonium thiosulphate, if desired with additives such as sodium bisulphite and/or sodium metabisulphite.

All the baths can contain additives, such as hardeners, wetting agents, optical brighteners and UV-stabilisers.

The process for the rapid processing of silver dye bleach materials can be used, for example, in the production of positive coloured images in automatic copying or recording machines or in the rapid processing of other silver dye bleach materials, such as, for example, for scientific recording and industrial purposes, for example coloured X-ray screen photography.

A transparent, metallic-reflecting material or, preferably, white-opaque material, the carrier of which is not able to absorb any liquid from the baths, can be used as the silver dye bleach material.

The carrier can consist, for example, of optionally pigmented cellulose triacetate or polyester. If it consists of a paper felt this must be lacquer-coated or coated with polyethylene on both sides. The light-sensitive layers are located on at least one side of this carrier, preferably in the known arrangement, that is to say at the bottom a red-sensitised silver halide emulsion layer which contains a cyan azo dyestuff, above this a green-sensitised silver halide emulsion layer which contains a magenta azo dyestuff and on the top a blue-sensitive silver halide emulsion layer which contains a yellow azo dyestuff. The material can also contain sub-layers, intermediate layers, filter layers and protective layers but the total thickness of the layers as a rule should not exceed 20μ.

Manufacturing instructions

General instruction A

Quinoxalines manufactured from an aromatic 1,2-diamine, ano-nitroaniline compound or ano-dinitrobenzene derivative and a 1,2-dicarbonyl compound A substituted o-dinitrobenzene derivative or the corresponding o-nitroaniline compound is dissolved, or merely suspended, in a suitable solvent such as, for example, ethyl acetate, methanol, ethanol, glacial acetic acid, dimethylformamide, 2-methoxyethanol, 2-ethoxyethanol or water, 1 to 10 per cent by weight of a hydrogenation catalyst, such as, for example, a 10% strength palladium-on-charcoal catalyst, are added and the hydrogenation is carried out under normal pressure, with initial warming if necessary. After the reaction has finished, the catalyst is filtered off under nitrogen and at least the equimolar amount of the corresponding diketone is added, under nitrogen, to the filtrate, which is cooled to 0° to 10° C. if necessary; in most cases a deepening of the colour takes place when this addition is made. The mixture is then stirred, with warming if necessary, until the reaction has ended and the desired substance is isolated. The product can be purified by recrystallisation from a suitable solvent, distillation or, if necessary, by chromatography or sublimation.

In some cases, sodium hyposulphite in alkaline solution is used as the reducing agent in order to reduce the o-dinitrobenzene derivative or the corresponding o-nitroaniline compound to the 1,2-diaminobenzene derivative.

If the corresponding o-phenylenediamine is easily accessible and in sufficient purity, it is, as described, subjected as such or in the form of its hydrochloride in a suitable solvent, under nitrogen, to a condensation reaction with the diketone. When the hydrochloride is used, it is advisable to add a corresponding amount of sodium acetate or potassium acetate, in order to neutralise the HCl liberated. The compounds which are obtained in this way are listed in Table I.

Preparation example A—1: (Comound No. 101)

2-(Bromomethyl)-6,7-dimethoxy-3-methyl-quinoxaline 11.4 g (50 mmols) of 1,2-dimethoxy-4,5-dinitrobenzene are dissolved in 100 ml of glacial acetic acid and, after adding 0.6 g of 10% strength palladium-on-characoal, hydrogenated under normal pressure; the temperature can rise to 60° C during the hydrogenation. Consumption of hydrogen: 7,300 ml (100% of theory). The catalyst is filtered off and the filtrate is cooled, under nitrogen, to 5° to 10° C. Whilst stirring well, 9 g (55 mmols) of 1-bromo-2,3-butanedione are added dropwise at 10° C. The solution is stirred for 60 minutes, during which time the desired product starts to precipitate out. The reaction mixture is discharged into 300 ml of cold water and the mixture is stirred for 10 minutes. The product which has precipitated is filtered off, washed with water and dried in vacuo at 60° C.

Yield: 10.7 g (72%)

Melting point: 164° to 165° C.

The IR and NMR spectra and the elementary analysis correspond to the indicated structure.

General instruction B

Quinoxalines manufactured by nucleophilic substitution from α-halogenomethylquinoxalines and Lewis bases:

An α-halogenomethylquinoxaline is dissolved, or merely suspended, in a suitable solvent, such as, for example, methanol, ethanol, 2-methoxyethanol, 2-ethoxyethanol, dimethylformamide, dimethylsulphoxide, acetonitrile, water, glycol, toluene, chlorobenzene, sulpholane or formamide. The Lewis base, optionally in a suitable solvent, is added to the solution or suspension of the α-halogenomethylquinoxaline, or a solution of the α-halogenomethylquinoxaline is added to the solution of the Lewis base. The mixture thus obtained is, if necessary, heated to the desired temperature and the substance formed is isolated. The product is purified by the customary processes.

The compounds which are manufactured according to these instructions are listed in Table II.

Preparation example B-1: (Compound No. 109)

2-(Hydroxymethyl)-6,7-dimethoxy-3-methyl-quinoxaline 8.9 g (30 mmols) of 2-(bromomethyl)-6,7-dimethoxy-3-methyl-quinoxaline are suspended in a mixture of 158 g (1.5 mols) of sodium carbonate, 350 ml of water and 100 ml of ethanol. The suspension is boiled under reflux for four hours. 300 ml of water are then added and the resulting mixture is extracted with three times 120 ml of chloroform. The organic phase is dried over magnesium sulphate. The solvent is evaporated in vacuo. The solid residue is recrystallised from methanol. This gives 3.5 g (50%) of a white powder.

Melting point: 176° to 177° C.

The IR and NMR spectra and the elementary analysis correspond to the indicated structure.

General instruction C

Sulphomethyl-substituted quinoxalines

An α-halogenomethylquinoxaline is suspended in a sodium sulphite or potassium sulphite solution (50% excess). The mixture is heated to the reflux temperature. After several hours, a virtually clear solution is obtained. The solution is filtered and the substance is optionally isolated in the form of the barium salt, the free acid is then liberated by adding the equimolar amount of sulphuric acid, the sodium salt is formed with the equimolar amount of sodium bicarbonate and the water is removed. If the barium salt does not precipitate, the water is removed in vacuo; subsequently the solid residue is extracted with a suitable solvent or, if necessary, isolated by chromatography.

The compounds obtained in this way are listed in Table III.

Preparation example C-1: (Compound No. 121)

7-Methyl-1,3-dioxolo-[4,5-g]-quinoxal-6-yl-methanesulphonic acid (sodium salt)

7.05 g (25 mmols) of 6-(bromomethyl)-7-methyl-1,3-dioxolo-[4,5-g]-quinoxaline are suspended in a mixture of 4.4 g (35 mmols) of sodium sulphite and 50 ml of water. The suspension is boiled under reflux for three hours. A virtually clear solution is obtained. The solution is filtered and half of the water is evaporated in vacuo. First 10 ml of acetic acid and then 6.11 g (25 mmols) of barium chloride in 20 ml of water are added. The mixture is heated to the reflux temperature; the desired barium salt then precipitates out. The suspension is cooled and the product is filtered off. The barium salt is dried at 80° C. in vacuo. 6.9 g (81% of theory) are obtained. This salt is suspended in water and the free acid is liberated by adding 1.05 g (10.15 mmols) of concentrated sulphuric acid in 20 ml of water. The mixture is heated to 80° C. for 15 minutes and the barium sulphate is then filtered off and washed with water. 1.71 g (20.3 mmols) of sodium bicarbonate are added to the filtrate. The solution is stirred for 15 minutes and then evaporated to dryness. The residue is dried at 80° C. in vacuo.

5.5 g (70% of theory) of the desired product are obtained.

The IR and NMR spectra correspond to the indicated structure. The product crystallises with half a mol of water.

Table I

| No. | Compound | Starting materials | | | Reducing agent | Isolation | Yield % | Melting point °C. |
|---|---|---|---|---|---|---|---|---|
| 101 | CH$_3$O—[quinoxaline]—CH$_2$Br, CH$_3$ | CH$_3$O—[benzene]—NO$_2$, CH$_3$O, NO$_2$ | CH$_3$—C(=O)—C(=O)—CH$_2$Br | | H$_2$/Pd—C acetic acid | filtration | 72 | 164–165 |
| 102 | [methylenedioxy-quinoxaline]—CH$_2$Br, CH$_3$ | [methylenedioxy-benzene]—NO$_2$, NO$_2$ | CH$_3$—C(=O)—C(=O)—CH$_2$Br | | H$_2$/Pd—C acetic acid | filtration | 80 | 174–175 |
| 103 | [ethylenedioxy-quinoxaline]—CH$_2$Br, CH$_3$ | [ethylenedioxy-benzene]—NO$_2$, NO$_2$ | CH$_3$—C(=O)—C(=O)—CH$_2$Br | | H$_2$/Pd—C acetic acid | filtration recrystallisation from (CH$_3$)$_2$CO/H$_2$O | 56 | 154–157 |
| 104 | [methylenedioxy-quinoxaline]—CH$_3$ | [methylenedioxy-benzene]—NO$_2$, NO$_2$ | CH$_3$COCOH | | H$_2$/Pd—C CH$_3$OCH$_2$CH$_2$OH | chromatography SiO$_2$/ CH$_3$COOC$_2$H$_5$ | 51 | 134–135 |

The NMR and infrared spectra of the products in this table correspond to the indicated structures.

Table II

| No. | Compound | Starting compound | Lewis base / Solvent | Isolation/purification | Yield (%) | (m.p.) Melting point/ (b.p.) boiling point °C. |
|---|---|---|---|---|---|---|
| 105 | 3,4-dimethoxyphenyl with N=C(CH$_2$CN)–C(CH$_3$)=N | 3,4-dimethoxyphenyl with N=C(CH$_2$Br)–C(CH$_3$)=N | KCN dimethylsulphoxide | chromatography SiO$_2$/ CH$_3$COOC$_2$H$_5$ | 15 | m.p. 204 |
| 106 | CH$_2$OCOCH$_3$ derivative | CH$_2$Br derivative | CH$_3$CO$_2$K ethanol | recrystallisation from toluene/n-C$_6$H$_{14}$ | 68 | m.p. 131–132 |
| 107 | CH$_2$OCH$_3$ derivative | CH$_2$Br derivative | CH$_3$ONa CH$_3$OH | recrystallisation from toluene/n-C$_6$H$_{14}$ | 64 | m.p. 101–102 |
| 108 | CH$_2$OCH$_2$CH$_2$OCH$_3$ derivative | CH$_2$Br derivative | CH$_3$OCH$_2$CH$_2$ONa CH$_3$OCH$_2$CH$_2$OH | distillation | 65 | b.p. 130 0.006 mm Hg m.p. 74–75 |
| 109 | CH$_2$OH derivative | CH$_2$Br derivative | H$_2$O/Na$_2$CO$_3$ ethanol | recrystallisation from methanol | 50 | m.p. 176–177 |
| 110 | CH$_2$SCH$_3$ derivative | CH$_2$Br derivative | CH$_3$SNa CH$_3$OCH$_2$CH$_2$OH | recrystallisation from methanol | 65 | m.p. 75–76 |
| 111 | CH$_2$CH$_2$SO$_2$CH$_3$ derivative | CH$_2$Br derivative | CH$_3$SO$_2$Na CH$_3$OCH$_2$CH$_2$OH | filtration | 86 | m.p. 222–223 |
| 112 | CH$_2$CH$_2$OCH$_2$CH$_2$OH derivative | CH$_2$Br derivative | HOCH$_2$CH$_2$ONa HOCH$_2$CH$_2$OH | recrystallisation from toluene | 60 | m.p. 98–102 |
| 113 | CH$_2$N(CH$_3$)$_2$ derivative | CH$_2$Br derivative | (CH$_3$)$_2$NH dimethylformamide | chromatography SiO$_2$/ CH$_3$COOC$_2$H$_5$ | 90 | m.p. 175–188 (decomposition) bis-hydrochloride |

Note: All starting compounds and products have the 3,4-dimethoxyphenyl-N=C(R)–C(CH$_3$)=N core structure, where R is the substituent shown.

Table II-continued

| No. | Compound | Starting compound | Lewis base Solvent | Isolation/purification | Yield (%) | (m.p.) Melting point/(b.p.) boiling point °C. |
|---|---|---|---|---|---|---|
| 114 | CH₃O—, CH₃O— benzene with N=C(CH₂PO(CH₃)₂)–N=C(CH₃) | CH₃O—, CH₃O— benzene with N=C(CH₂Br)–N=C(CH₃) | P(OCH₃)₃ chlorobenzene | chromatography SiO₂/ CH₃COOC₂H₅— —CH₃OH) | 60 | m.p. 132–134 |
| 115 | methylenedioxy-benzene with N=C(CH₂OH)–N=C(CH₃) | methylenedioxy-benzene with N=C(CH₂Br)–N=C(CH₃) | H₂O/K₂CO₃ dimethylformamide | via the hydrochloride or chromatography | 45 | m.p. 157–160 |
| 116 | methylenedioxy-benzene with N=C(CH₂SO₂CH₃)–N=C(CH₃) | methylenedioxy-benzene with N=C(CH₂Br)–N=C(CH₃) | CH₃SO₂Na CH₃OCH₂CH₂OH | filtration | 88 | m.p. 286–288 |
| 117 | ethylenedioxy-benzene with N=C(CH₂OH)–N=C(CH₃) | ethylenedioxy-benzene with N=C(CH₂Br)–N=C(CH₃) | H₂O/K₂CO₃ acetonitrile | chromatography SiO₂/ CH₃COOC₂H₅ | 28 | m.p. 169–171 |
| 118 | ethylenedioxy-benzene with N=C(CH₂SO₂CH₃)–N=C(CH₃) | ethylenedioxy-benzene with N=C(CH₂Br)–N=C(CH₃) | CH₃SO₂Na CH₃OCH₂CH₂OH | recrystallisation from dimethylformamide/water | 70 | m.p. 242–244 |

Compound 113 is isolated in the form of the bis-hydrochloride; the compound is strongly hygroscopic. The NMR and infrared spectra of the products in this table correspond to the indicated structures.

TABLE III

| No. | Compound | Starting compound | Isolation/purification | Yield % | Melting point °C. | Remarks |
|---|---|---|---|---|---|---|
| 119 | CH₃O-quinoxaline-CH₂SO₃Na / CH₃ (6,7-dimethoxy) | CH₃O-quinoxaline-CH₂Br / CH₃ | extraction with dimethylsulphoxide | 75 | >280 | crystallises with one mol of H₂O titre ≈ 75% (contains NaBr) |
| 120 | 6,7-dimethoxy quinoxaline-2,3-bis(CH₂SO₃Na) | 6,7-dimethoxy quinoxaline-2,3-bis(CH₂Br) | via the barium salt | 80 | — | crystallises with 3 mols of H₂O |
| 121 | methylenedioxy quinoxaline-CH₂SO₃Na/CH₃ | methylenedioxy quinoxaline-CH₂Br/CH₃ | via the barium salt | 70 | — | crystallises with half a mol of H₂O |
| 122 | ethylenedioxy quinoxaline-CH₂SO₃Na/CH₃ | ethylenedioxy quinoxaline-CH₂Br/CH₃ | chromatography SiO₂/dimethylformamide | 81 | — | crystallises with one mol of H₂O titre ≈ 75% (contains NaBr) |

The NMR and infrared spectra of the products in this table correspond to the indicated structures.

APPLICATION EXAMPLES

EXAMPLE 1

The effectiveness of the new quinoxalines as silver dye bleach catalysts is examined with the aid of single layer coatings of the following composition:

8.2 g of gelatine/m²
Molar ratio of silver to dyestuff: 44:1
Maximum transmission density of the dyestuff about 1.4.

The silver halide emulsion used is a bromide/iodide emulsion which contains 2.6 mol% of iodine and has not been spectrally sensitised. One of the following dyestuffs is used:

Yellow:

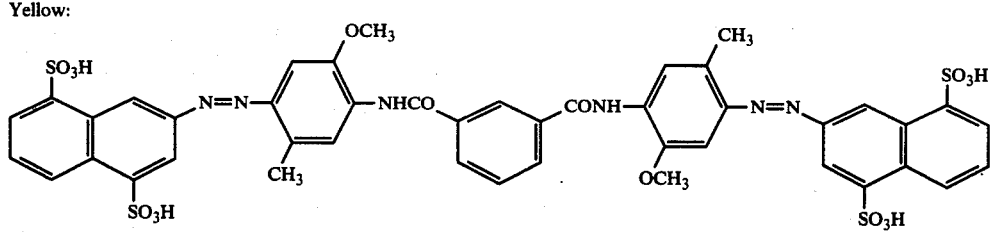
(123)

Magenta:

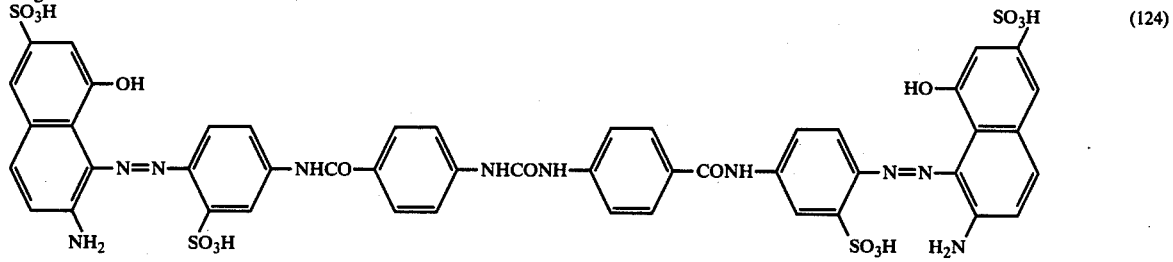
(124)

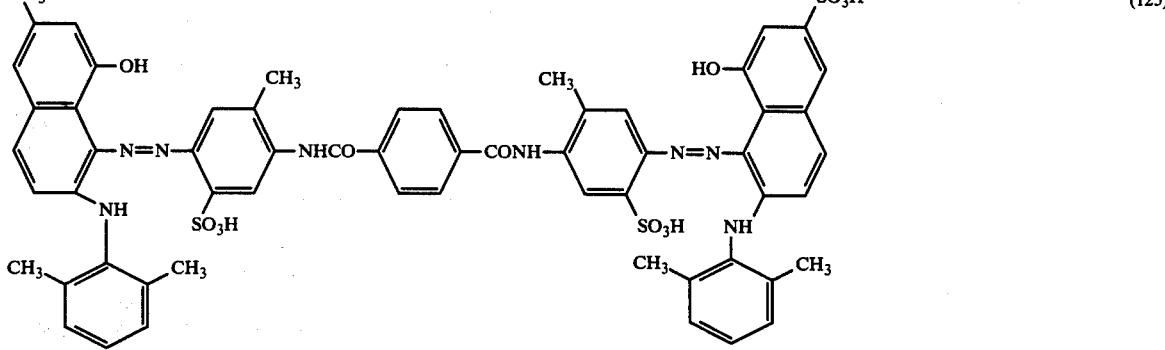
(125)

Cyan:

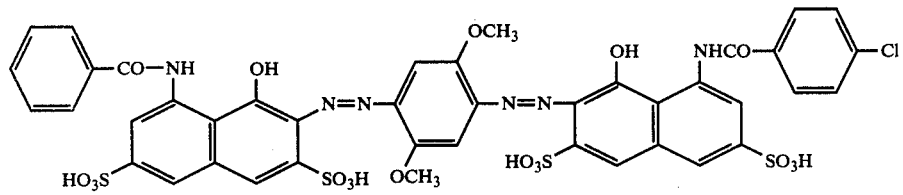
(126)

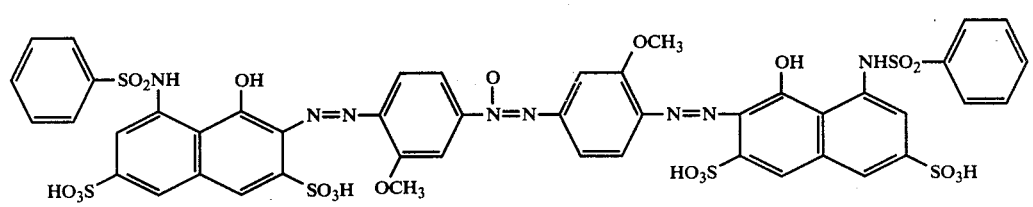
(127)

Coatings, which correspond to the above data, on opaque triacetate film are exposed behind a step wedge and then processed at 24° C., as follows:

| | |
|---|---|
| Developing bath | 6 minutes |
| Washing | 4 minutes |
| Dye bleach bath | 7 minutes |
| Washing | 2 minutes |
| Silver bleach bath | 2 minutes |
| Washing | 2 minutes |
| Fixing bath | 8 minutes |
| Washing | 6 minutes |

Drying

A conventional black-and-white developer is used in the developing bath and baths of customary composition are also used as the silver bleach bath and the fixing bath. The dye bleach bath contains the following components: 28 ml of concentrated sulphuric acid, 1 ml of thioglycerol, 9 g of sodium iodide and 1 mmol of the dye bleach catalyst of the formula (104), per litre of solution.

As a result of processing, a sharp yellow or magenta or cyan step wedge is obtained, depending on the dyestuff. Similar results are also obtained with other catalysts of Tables I to III.

EXAMPLE 2

Single layer coatings according to Example 1 are exposed behind a step wedge and then processed at 24° C., as follows:

| | |
|---|---|
| Developing bath | 6 minutes |
| Washing | 4 minutes |
| Bleach bath | 6 minutes |
| Washing | 2 minutes |
| Fixing bath | 8 minutes |
| Washing | 6 minutes |

Drying

A conventional black-and-white developer is used in the developing bath and baths of customary composition are also used as the silver bleach bath and the fixing bath. The dye bleach bath contains the following components: 28 ml of concentrated sulphuric acid, 1 ml of thioglycerol, 9 g of sodium iodide and 1 mmol of the dye bleach catalyst of the formula (104), per litre of solution.

As a result of processing, a sharp yellow or magenta or cyan step wedge is obtained, depending on the dyestuff. Similar results are also obtained with other catalysts of Tables I to III.

EXAMPLE 2

Single layer coatings according to Example 1 are exposed behind a step wedge and then processed at 24° C., as follows:

| | |
|---|---|
| Developing bath | 6 minutes |
| Washing | 4 minutes |
| Bleach bath | 6 minutes |
| Washing | 2 minutes |
| Fixing bath | 8 minutes |
| Washing | 6 minutes |

Drying

A conventional black-and-white developer is used as the developing bath and a conventional fixing bath is used as the fixing bath. The bleach bath contains the following components: 28 ml of concentrated sulphuric acid, 1 ml of thioglycerol, 9 g of sodium iodide, 10 mmols of 2-nitrotoluene-4-sulphonic acid and 5 mmols of the catalyst of the formula (120), per litre of solution.

As a result of processing, a sharp yellow or magenta or cyan step wedge is obtained, depending on the dyestuff. Analogous results are also obtained with other combinations of the catalysts from Tables I to III and the oxidising agents of the formula (17).

EXAMPLE 3

A photographic material with three colour layers for the silver dye bleach process is prepared on a cellulose acetate carrier; it contains, in the lowest, red-sensitive layer, the cyan image dyestuff of the formula

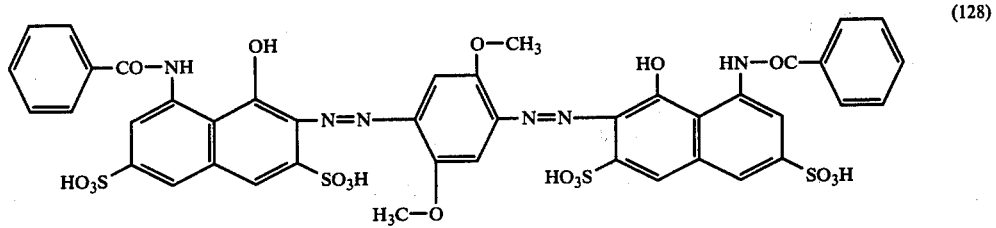

(128)

in the green-sensitive layer, above the preceding layer, the magenta image dyestuff of the formula (124) and in the uppermost, blue-sensitive layer, the yellow image dyestuff of the formula (123).

The image dyestuffs are incorporated into the emulsions so as to give a reflection density of D = 2.0. The colour layers, containing a total of 0.8 g of Ag/m$^2$, are separated by gelatine layers and the total thickness is 15μ.

This material is exposed behind a step wedge and then processed as follows:

1. Silver developing bath

| | |
|---|---|
| Sodium polyphosphate | 2 g/l |
| Anhydrous sodium sulphite | 50 g/l |
| Hydroquinone | 6 g/l |
| Sodium metaborate | 15 g/l |
| Borax | 15 g/l |
| 1-Phenyl-3-pyrazolidinone | 0.25 g/l |
| Potassium bromide | 1 g/l |
| Benztriazole | 0.1 g/l |

2. Bleach bath

| | |
|---|---|
| 96% strength sulphuric acid | 28 ml/l |
| Thioglycerol | 1 ml/l |
| Sodium iodide | 9 g |
| 2-Amino-4-methyl-5-nitrobenzene-sulphonic acid (ammonium salt) | 5 g/l |
| Catalyst: compound of the formula (115) | 1.1 g/l |

3. Fixing bath

| | |
|---|---|
| 60% strength ammonium thiosulphate | 315 ml/l |
| 60% strength ammonium bisulphite | 46 ml/l |
| 25% strength ammonia (aqueous solutions each) | 20 ml/l |

4. Washing

After drying, a clear neutral grey image of the subject used is obtained, the exposed regions having been bleached to pure white. Similar results are obtained when other combinations of the catalysts from Tables I to III and the oxidising agent of the formula (17) are employed in corresponding amounts.

EXAMPLE 4

A photographic material for the silver dye bleach process is prepared on a pigmented cellulose acetate carrier using the cyan image dyestuff of the formula (128) with the magenta image dyestuff of the formula (124) and the yellow image dyestuff of the formula (123).

The material is made up of double layers, as follows (compare German Offenlegungsschrift 2,036,918):

| |
|---|
| blue-sensitive, colourless |
| blue-sensitive, yellow dyestuff (123) |
| yellow filter |
| green-sensitive, colourless |
| green-sensitive, magenta dyestuff (124) |
| intermediate layer (gelatine) |
| red-sensitive, cyan dyestuff (128) |
| red-sensitive, colourless |
| carrier, opaque |

The image dyestuffs are incorporated into the coatings so as to give a reflection density of D = 2.0. The total silver content of the photographic layers, whose total thickness amounts to 22 μ, is 2.0 g of Ag/m$^2$.

In an enlarger, an image of a coloured transparency is projected onto the material. Processing is then carried out in accordance with the following instructions (bath temperature 24° C.):

1. Silver developing bath : 2 minutes
Composition

| | |
|---|---|
| Sodium polyphosphate | 1 g/l |
| Anhydrous sodium sulphite | 40 g/l |
| Hydroquinone | 10 g/l |
| Sodium metaborate | 20 g/l |
| Sodium hydroxide | 3 g/l |
| 1-Phenyl-3-pyrazolidinone | 1 g/l |
| Potassium bromide | 1.5 g/l |
| Benztriazole | 0.2 g/l |

2. Bleach bath: 4 minutes
Composition

| | |
|---|---|
| Sulphamic acid | 100 g/l |
| Ascorbic acid | 2 g/l |
| Ammonium iodide | 7 g/l |
| Sodium salt of m-nitrobenzene-sulphonic acid | 10 g/l |

Catalyst:
Compound of the formula (104) 3 g/l

3. Fixing bath : 4 minutes
Composition
Ammonium thiosulphate 220 g

Sodium metabisulphite 10 g

Sodium sulphite 40 g

4. Washing : 6 minutes
Total processing time 16 minutes

After drying, a print of the colour transparency is obtained which is true in colour and tonality.

Similar results can be achieved when a bleach bath is used which, for example, is prepared from two liquid concentrates according to the following instructions:
Composition of the solution used (1 l):
Water 800 ml Part A 100 ml Part B 100 ml Composition part A:
96% strength sulphuric acid 20 ml The sodium salt of m-nitrobenzene-sulphonic acid 7 g Water to make up to 100 ml Composition part B:
Ethylene glycol monoethyl ether 65 ml Catalyst:
Compound of the formula (104) 3 g Ascorbic acid 3 g Potassium iodide 6 g Water to make up to 100 ml The other compounds given in Tables I to II can also be employed as catalysts, in place of the compound of the formula (104), with an equally good result.

EXAMPLE 5

The photographic material has the composition described in Example 4.

The image dyestuffs are incorporated into the emulsions so as to give a reflection density of D = 2.0. The colour layers, containing a total of 0.8 g of Ag/m$^2$, are separated by gelatine layers and the total thickness of the 8 layers is 15 $\mu$.

This material is exposed in a reproduction camera and then processed in a so-called roll processor. This apparatus consists of 4 tanks, each of 2 liters capacity. The speed of the drive system is so adjusted that the immersion time per tank is 60 seconds. The exposed material passes through the 4 tanks containing the following processing solutions and the temperature of the baths is 35° C:
1st tank - silver developing bath
Composition Sodium polyphosphate 1 g/l Anhydrous sodium sulphite 40 g/l Hydroquinone 10 g/l Sodium metaborate 20 g/l Sodium hydroxide 3 g/l 1-Phenyl-3-pyrazolidinone 1 g/l Potassium bromide 1.5 g/l Benztriazole 0.2 g/l Catalyst:
Compound of the formula (109) 0.4 g/l 2nd tank — bleach bath
Composition
96% strength sulphuric acid 20 ml/l 4-Mercaptobutyric acid 1 ml/l Potassium iodide 10 g Sodium salt of m-nitrobenzene-sulphonic acid 7 g Catalyst:
Compound of the formula (109) 2 g 3rd tank — fixing bath
Composition
Ammonium thiosulphate 220 g Sodium metabisulphite 10 g Sodium sulphite 40 g 4th tank — washing bath
Total processing time
(including transport time from tank to tank and with equal dwell time of about 1 minute in the individual tanks). 5 minute After drying, reproductions of the recorded subject are obtained which are true to nature in colour and tonality. With one filling of the tank it is possible to develop 40 to 60 images 18 cm × 24 cm in size in the course of 14 days; the quality of the images is virtually unchanged.

The other compounds given in Tables I to III can also be employed, in place of the compound of the formula (109), with an equally good result.

What is claimed is:

1. Process for the production of colored photographic images by the silver dye bleach process which comprises the steps of imagewise exposing a photographic material containing on a substrate, at least one silver halide emulsion layer with a bleachable dyestuff, then (1) developing the silver image obtained, (2) dye bleaching and silver bleaching said silver image, (3) silver fixing and (4) washing, said dye and/or silver bleaching step being carried out in a bath containing at least one bleach catalyst of the formula

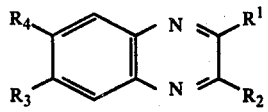

in which $R_1$ is hydrogen, —$CH_2OR$, —$CH_2NRR'$, —$CH_2OCOR$, —$CH_2Cl$, —$CH_2Br$, —$CH_2CN$, —$CH_2SR$, —$CH_2SCN$, —$CH_2O(CH_2)_mOR$, —$CH_2(OCH_2CH_2)_nOR$, —$CH_2SO_2B_5$, —$CH_2PO(OR_5)_2$, —$CH_2SO_3R_6$ or —$CH_2PO(OR_6)_2$, $R_1$ being hydrogen only when $R_3$ and $R_4$ conjointly are —$O(CH_2)_pO$—, and $R_2$ is methyl and —$CH_2PO(OR_5)_2$, —$CH_2PO(OR_6)_2$ or $CH_2SO_3R_6$, and $R_3$ and $R_4$ independently are alkyl with 1 to 5 carbon atoms, alkoxy with 1 to 4 carbon atoms, $RO(CH_2)_mO$— or $RO(CH_2CH_2O)_n$— or $R_3$ and $R_4$ conjointly are —$O(CH_2)_pO$—, R and R' independently are hydrogen or alkyl with 1 to 4 carbon atoms, $R_5$ is alkyl with 1 to 4 carbon atoms, $R_6$ is hydrogen, an alkali metal cation or —$N^\oplus(R)_4$, m is 3 or 4, n is 1 to 3 and p is 1 or 2.

2. Process according to claim 1, wherein $R_3$ and $R_4$ independently — are alkyl with 1 to 5 carbon atoms or alkoxy with 1 to 4 carbon atoms, or $R_3$ and $R_4$ conjointly are —$O(CH_2)_pO$ 3. Process according to claim 1, wherein the bleach catalyst corresponds to the formula

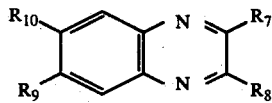

in which $R_7$ is hydrogen if $R_9$ and $R_{10}$ conjointly are —$O(CH_2)_pO$—or is —$CH_2OR_{11}$, —$CH_2NR_{11}R'_{11}$, —$CH_2OCOR_{11}$, —$CH_2OCH_2CH_2OR_{11}$, —$CH_2SO_3R_6$, —$CH_2Br$, —$CH_2SR_{11}$, —$CH_2SO_2CH_3$, —$CH_2PO(OCH_3)_2$ or —$CH_2PO(OR_6)_2$ and $R_8$ is methyl or —$CH_2SO_3$, $R_6$, $R_9$ and $R_{10}$ independently are alkoxy with 1 to 4 carbon atoms, or $R_9$ and $R_{10}$ conjointly are —$O(CH_2)_pO$—, $R_{11}$ and $R'_{11}$ are hydrogen or methyl.

4. Process according to claim 3, wherein the bleach catalyst corresponds to the formula

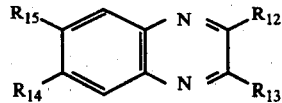

in which $R_{12}$ is hydrogen if $R_{14}$ and $R_{15}$ conjointly are —$O(CH_2)_pO$— or is —$CH_2OH$ or —$CH_2SO_3R_6$ and $R_{13}$ is methyl or —$CH_2SO_3R_6$, $R_{14}$ and $R_{15}$ are methoxy, or $R_{14}$ and $r_{15}$ conjointly are —$O(CH_2)_pO$—.

5. Process according to claim 1, wherein the treatment stages (1) to (4) are used in the sequence (1) to (4), wherein the bleach bath (2) for the combined dye bleaching and silver bleaching contains (a) a strong acid, (b) a water-soluble iodide, (c) a water-soluble oxidising agent, (d) an antioxidant and (e) a bleach catalyst according to claim 1 and (f) optionally a bleach accelerator and the entire processing, from entry into the first bath (1) to leaving the final bath, is carried out at temperatures of 20 to 90° C.

6. Process according to claim 5, wherein the entire processing, from entry into the first bath (1) to leaving the final bath, takes at most 10 minutes and the dwell time in the individual processing tanks is at most 2 minutes.

7. Aqueous formulation for dye bleaching and/or silver bleaching which contains (a) a strong acid, (b) a water-soluble iodide, (c) a water-soluble oxidising agent, (d) an antioxidant, (e) a bleach catalyst and, optionally, (f) a bleach accelerator, wherein the bleach catalyst is a quinoxaline of the formula

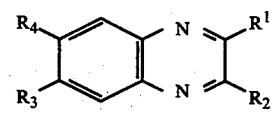

in which $R_1$ is hydrogen, —$CH_2OR$, —$CH_2NRR'$, —$CH_2OCOR$, —$CH_2Cl$, —$CH_2Br$, —$CH_2CN$, —$CH_2SR$, —$CH_2SCN$, —$CH_2O(CH_2)_mOR$, —$CH_2(OCH_2CH_2)_nOR$, —$CH_2SO_2R_5$, $CH_2PO(OR_5)_2$, —$CH_2SO_3R_6$ or —$CH_2PO(OR_6)_2$, $R_1$ being hydrogen only when $R_3$ and $R_4$ conjointly are —$O(CH_2)_pO$—, and $R_2$ is methyl and —$CH_2PO(OR_5)_2$, —$CH_2PO(OR_6)_2$ or $CH_2SO_3R_6$, $R_3$ and $R_4$ independently are alkyl with 1 to 5 carbon atoms, alkoxy with 1 to 4 carbon atoms, $RO(CH_2)_mO$— or $RO(CH_2CH_2O)_n$— or $R_3$ and $R_4$ conjointly are —$O(CH_2)_pO$—, R and R' independently are hydrogen or alkyl with 1 to 4 carbon atoms, $R_5$ is alkyl with 1 to 4 carbon atoms, $R_6$ is hydrogen, an alkali metal cation or —$N^\oplus(R)_4$, m is 3 or 4, n is 1 to 3 and p is 1 or 2.

8. Aqueous formulation according to claim 7, which contains 0.5 to 5 g/l of the bleach catalyst.

9. A photographic bleach bath or a combined dye bleach and silver bleach bath, for the silver dye bleach process, which contains, as the bleach catalyst, at least one quinoxaline of the formula

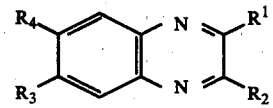

in which $R_1$ is hydrogen, —$CH_2OR$, —$CH_2NRR'$, —$CH_2OCOR$, —$CH_2Cl$, —$CH_2Br$, —$CH_2CN$, —$CH_2SR$, —$CH_2SCN$, —$CH_2O(CH_2)_mOR$, —$CH_2(OCH_2CH_2)_nOR$, —$CH_2SO_2R_5$, $CH_2PO(OR_5)_2$, —$CH_2OR_3R_6$ or —$CH_2PO(OR_6)_2$ $R_1$ being hydrogen only when $R_3$ and $R_4$ conjointly are —$O(CH_2)_pO$—, and $R_2$ is methyl and -$CH_2PO(OR_5)_2$, —$CH_2PO(OR_6)_2$ or $CH_2SO_3R_6$, $R_3$ and $R_4$ independently are alkyl with 1 to 5 carbon atoms, alkoxy with 1 to 4 carbon atoms, $RO(CH_2)_mO$— or $RO(CH_2CH_2O)_n$—or $R_3$ and $R_4$ conjointly are —$O(CH_2)_pO$—, R and R' independently are hydrogen or alkyl with 1 to 4 carbon atoms, $R_5$ is alkyl with 1 to 4 carbon atoms, $R_6$ is hydrogen, an alkali metal cation or —$N^\oplus(R)_4$, m is 3 or 4, n is 1 to 3 and p is 1 or 2.

* * * * *

UNITED STATES PATENT AND TRADEMARK OFFICE
CERTIFICATE OF CORRECTION

PATENT NO. : 4,145,217
DATED : March 20, 1979                    Page 1 of 2
INVENTOR(S) : Gerald Jan, et al.

It is certified that error appears in the above-identified patent and that said Letters Patent are hereby corrected as shown below:

Column 1, line 68, "isoamly" should be --isoamyl--.

Column 8, line 49, "Bdenotes" should be --B denotes--.

Column 10, line 17, "characoal" should be --charcoal--.

Column 14, No. 111, "$CH_2CH_2So_2CH_3$" should be --$CH_2SO_2CH_3$--.

Column 19, line 64 move --2 minutes-- to the right

Column 24, line 47, delete "5 minutes" on line 47 and insert --5 minutes-- on line 44 after "Total Processing Time".

Column 24, line 62 "on" should be --one--.

UNITED STATES PATENT AND TRADEMARK OFFICE
CERTIFICATE OF CORRECTION

PATENT NO. : 4,145,217
DATED : March 20, 1979
INVENTOR(S) : Gerald Jan, et al.

It is certified that error appears in the above-identified patent and that said Letters Patent are hereby corrected as shown below:

Column 25, line 11 "$-CH_2SO_2{}^B5$" should be --$CH_2SO_2R_5$--.

Column 25, line 54 "r15" should be --$R_{15}$--.

Column 26, line 6, " 2minutes" should be --2 minutes--.

Column 26, line 61 "$N\oplus$" should be --$N^{\oplus}$--.

Column 25, line 25, "$-O(CH_2)_pO$" should be
-- $-O(CH_2)_pO-$, --.

Signed and Sealed this

Twenty-fourth Day of July 1979

[SEAL]

Attest:

LUTRELLE F. PARKER
Attesting Officer    Acting Commissioner of Patents and Trademarks